US00PP17955P2

(12) United States Plant Patent
Westhoff

(10) Patent No.: US PP17,955 P2
(45) Date of Patent: Aug. 28, 2007

(54) *CALIBRACHOA* PLANT NAMED 'WESCAOSU'

(50) Latin Name: ***Calibrachoa* sp.**
Varietal Denomination: Wescaosu

(75) Inventor: Heinrich Westhoff, Südlohn (DE)

(73) Assignee: J. + H. Westhoff Interpel, Südlohn (DE)

( * ) Notice: Subject to any disclaimer, the term of this patent is extended or adjusted under 35 U.S.C. 154(b) by 0 days.

(21) Appl. No.: 11/358,891

(22) Filed: Feb. 17, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Calibrachoa* plant named 'Wescaosu', characterized by its upright to cascading and vigorous growth habit; short internodes and freely branching habit; dense and bushy appearance; medium-sized leaves; medium-sized flowers; and numerous orange and red bi-colored flowers.

1 Drawing Sheet

Botanical designation: *Calibrachoa* sp.
Cultivar denomination: 'Wescaosu'.

BACKGROUND OF THE INVENTION

The present Invention relates to a new and distinct cultivar of *Calibrachoa* plant, botanically known as *Calibrachoa* sp., and hereinafter referred to by the cultivar name 'Wescaosu'.

The new *Calibrachoa* is a product of a planned breeding program conducted by the Inventor in Südlohn, Germany. The objective of the breeding program is to develop new vigorous *Calibrachoa* cultivars with attractive and unique flower coloration.

The new *Calibrachoa* originated from a cross-pollination made by the Inventor in 2003 of a proprietary selection of *Calibrachoa* identified as code number 03P915, not patented, as the female, or seed, parent with a proprietary selection of *Calibrachoa* identified as code number 03P816, not patented, as the male, or pollen, parent. The new *Calibrachoa* was discovered and selected by the Inventor in a controlled environment in Südlohn, Germany as a single plant within the resulting progeny from the stated cross-pollination.

Asexual reproduction of the new cultivar by terminal cuttings at Südlohn, Germany since 2004, has shown that the unique features of this new *Calibrachoa* are stable and reproduced true to type in successive generations.

SUMMARY OF THE INVENTION

Plants of the cultivar Wescaosu have not been observed under all possible environmental conditions. The phenotype may vary with variations in environment such as temperature and light intensity without, however, any variance in genotype.

The following traits have been repeatedly observed and are determined to be the unique characteristics of 'Wescaosu'. These characteristics in combination distinguish 'Wescaosu' as a new and distinct cultivar of *Calibrachoa:*

1. Upright to cascading and vigorous growth habit.
2. Short internodes and freely branching habit; dense and bushy appearance.
3. Medium-sized leaves.
4. Medium-sized flowers.
5. Numerous orange and red bi-colored flowers.

Plants of the cultivar Wescaosu can be compared to plants of the female parent selection. In side-by-side comparisons conducted in Südlohn, Germany, plants of the new *Calibrachoa* differed from plants of the female parent selection in the following characteristics:

1. Plants of the new *Calibrachoa* were more compact than plants of the female parent selection.
2. Plants of the new *Calibrachoa* and the female parent selection differed in flower color as plants of the female parent selection had yellow-colored flowers with red-colored venation.

Plants of the cultivar Wescaosu can be compared to plants of the male parent selection. In side-by-side comparisons conducted in Südlohn, Germany, plants of the new *Calibrachoa* differed from plants of the male parent selection in the following characteristics:

1. Plants of the new *Calibrachoa* had smaller leaves than plants of the male parent selection.
2. Plants of the new *Calibrachoa* had smaller flowers than plants of the male parent selection.
3. Plants of the new *Calibrachoa* and the male parent selection differed in flower color as plants of the male parent selection had red-colored flowers.

Plants of the new *Calibrachoa* can also be compared to plants of the *Calibrachoa* cultivar Wescaora, disclosed in U.S. Plant Pat. No. 14,822. In side-by-side comparisons conducted in Südlohn, Germany, plants of the new *Calibrachoa* differed from plants of the cultivar Wescaora in the following characteristics:

1. Plants of the new *Calibrachoa* were more mounding than plants of the cultivar Wescaora.
2. Plants of the new *Calibrachoa* had smaller leaves than plants of the cultivar Wescaora.

3. Plants of the new *Calibrachoa* and the cultivar Wescaora differed in flower color as plants of the cultivar Wescaora had yellow orange-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of a typical flowering plant of 'Wescaosu' grown in a container.

The photograph at the bottom of the sheet is a close-up view of a typical flower of 'Wescaosu'.

DETAILED BOTANICAL DESCRIPTION

Plants used in the aforementioned photographs and for the following description were grown under conditions which closely approximate commercial production conditions during the spring and summer in a glass-covered greenhouse in Südlohn, Germany. Plants were about 22 weeks from planting rooted cuttings and grown in containers. During the production of the plants, the day temperatures ranged from 20° C. to 25° C., night temperatures ranged from 16° C. to 18° C. and light levels ranged from 3,000 to 50,000 lux. In the following description, color references are made to The Royal Horticultural Society Colour Chart, 2001 Edition, except where general terms of ordinary dictionary significance are used.

Botanical classification: *Calibrachoa* sp. cultivar Wescaosu.

Parentage:

*Female parent.*—Proprietary selection of *Calibrachoa* sp. identified as 03P915, not patented.

*Male parent.*—Proprietary selection of *Calibrachoa* sp. identified as 03P816, not patented.

Propagation:

*Type cutting.*—Terminal vegetative cuttings.

*Time to initiate roots.*—About 18 to 20 days at 20° C.

*Time to develop roots.*—About 20 to 28 days at 20° C.

*Root description.*—Fine, fibrous.

*Rooting habit.*—Freely branching.

Plant description:

*Form.*—Annual flowering plant; upright to cascading; uniformly mounded; plants eventually become spherical in overall shape. Freely branching with lateral branches forming at every node. Vigorous growth habit.

*Usage.*—Appropriate for hanging baskets, window boxes and patio containers.

*Plant height (from soil level to top of plant plane).*—About 17.3 cm.

*Plant length (from soil level to lateral branches apices).*—About 40 cm to 50 cm.

*Stem description.*—Main branches, length: About 31 cm. Main branches, diameter: About 2 mm. Lateral branches, length: About 16.7 cm. Lateral branches, diameter: About 1.1 mm. Internode length: About 1.6 cm. Texture: Densely pubescent. Strength: Strong, wiry. Color: 146C.

*Foliage description.*—Arrangement: Alternate, simple; sessile. Length: About 2.9 cm. Width: About 1.2 cm. Shape: Broadly ovate to elliptic. Apex: Obtuse. Base: Attenuate. Margin: Entire. Texture, upper and lower surfaces: Pubescent. Venation: Pinnate. Color: Developing foliage, upper and lower surfaces: 147B. Fully expanded foliage, upper surface: 147A; venation, 147A to 147B. Fully expanded foliage, lower surface: 147B; venation, 147B to 147C.

Flower description:

*Flower type and habit.*—Medium-sized flowers; flowers face upright or outward; single, axillary. Flowers not persistent. Freely flowering with flowers forming at every axil.

*Natural flowering season.*—Spring until frost in the autumn; flowering continuous.

*Flower longevity on the plant.*—About one week.

*Flower size.*—Diameter: About 3 cm. Depth (height): About 1.9 cm. Tube length: About 1.5 cm. Throat diameter, distal end: About 7.5 mm. Tube diameter, proximal end: About 2 mm.

*Flower buds.*—Length: About 2.2 cm. Diameter: About 3.7 mm. Shape: Oblong. Color: Towards the base, 145A to 145B: towards the apex, 34D.

*Corolla.*—Arrangement/appearance: Single whorl of five petals, fused into flared trumpet. Petal length from throat: About 1.3 cm. Petal width: About 1.4 cm. Petal shape: Roughly spatulate with an obtuse apex. Petal margin: Entire. Petal texture, upper and lower surfaces: Smooth, glabrous; satiny. Color: Petal, when opening, upper surface: Towards the margins, 47A; center, 32A to 32B; towards the center, 44A to 44B. Petal, when opening, lower surface: 29C to 29D; venal areas, 48B to 48D. Petal, fully opened, upper surface: Center and towards the margins, 32A to 33B; color becoming closer to 32C with development; towards the center, 44B; color becoming closer to 44C with development; venation, 53A. Petal, fully opened, lower surface: 24C to 24D; venal areas, 48A to 48B; venation, 187A. Flower throat (inside): 13A; venation, 166A. Flower tube (outside): 4A; venation, 166A.

*Sepals.*—Arrangement/appearance: Single whorl of five sepals, star-shaped. Length: About 1.6 cm. Width: About 3.1 mm. Shape: Lanceolate. Apex: Rounded. Margin: Entire. Texture, upper and lower surfaces: Pubescent. Color, upper and lower surfaces: 137A.

*Peduncles.*—Length: About 1.9 cm. Width: About 1.1 mm. Strength: Flexible, wiry. Texture: Densely pubescent. Color: 146B.

*Reproductive organs.*—Stamens: Quantity per flower: Five. Anther shape: Four-parted, ovate. Anther length: About 1.6 mm. Anther diameter: About 1.5 mm. Anther color: 12B. Pollen amount: Moderate. Pollen color: 13B. Pistils: Quantity per flower: One. Pistil length: About 1.2 cm. Stigma shape: Ovate. Stigma color: 144A. Style length: About 8 mm. Style color: 145B. Ovary color: 145A.

*Seed/fruit.*—Seed and fruit production has not been observed.

Disease/pest resistance: Plants of the new *Calibrachoa* have not been noted to be resistant to pathogens and pests common to *Calibrachoa.*

Temperature tolerance: Plants of the new *Calibrachoa* have been observed to be tolerant to temperatures ranging from about 4° C. to about 30° C.

It is claimed:

1. A new and distinct cultivar of *Calibrachoa* plant named 'Wescaosu', as illustrated and described.

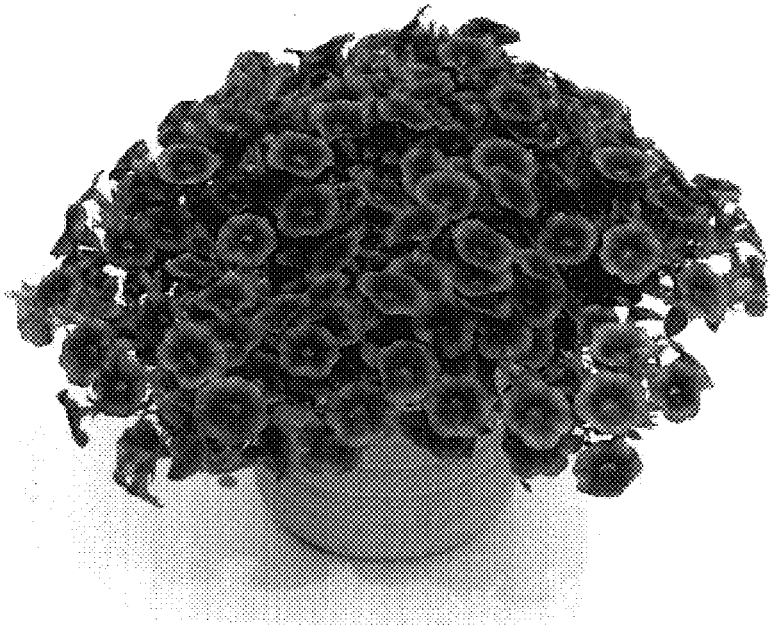
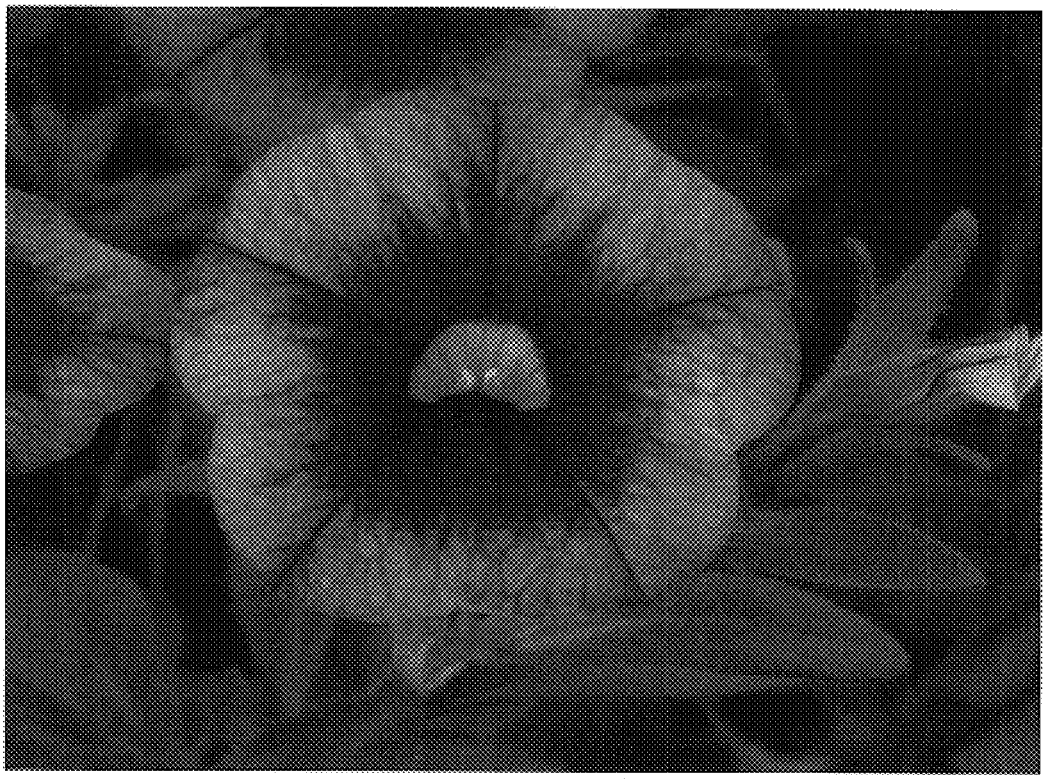

* * * * *